US011805996B2

(12) United States Patent
Bicocchi

(10) Patent No.: US 11,805,996 B2
(45) Date of Patent: Nov. 7, 2023

(54) CONTAINER AND METHOD FOR PRESERVING A TISSUE SAMPLE

(71) Applicant: Enrico Bicocchi, Leghorn (IT)

(72) Inventor: Enrico Bicocchi, Leghorn (IT)

( * ) Notice: Subject to any disclaimer, the term of this patent is extended or adjusted under 35 U.S.C. 154(b) by 741 days.

(21) Appl. No.: 16/762,005

(22) PCT Filed: Nov. 8, 2018

(86) PCT No.: PCT/IB2018/058789
§ 371 (c)(1),
(2) Date: May 6, 2020

(87) PCT Pub. No.: WO2019/092638
PCT Pub. Date: May 16, 2019

(65) Prior Publication Data
US 2020/0318043 A1 Oct. 8, 2020

(30) Foreign Application Priority Data

Nov. 8, 2017 (IT) .......................... 102017000125147

(51) Int. Cl.
*A61B 10/00* (2006.01)
*C12M 3/00* (2006.01)
*C12M 1/02* (2006.01)
*C12M 1/00* (2006.01)

(52) U.S. Cl.
CPC ......... *A61B 10/0096* (2013.01); *C12M 21/08* (2013.01); *C12M 23/44* (2013.01); *C12M 27/00* (2013.01); *C12M 29/20* (2013.01)

(58) Field of Classification Search
None
See application file for complete search history.

(56) References Cited

U.S. PATENT DOCUMENTS

| 2008/0290050 | A1* | 11/2008 | Reis, Jr. | ............... A61L 27/3834 |
| | | | | 210/348 |
| 2017/0265847 | A1* | 9/2017 | Cortelazzo | .............. B01L 3/508 |
| 2017/0369833 | A1* | 12/2017 | Kamiya | ................. C12M 23/46 |

FOREIGN PATENT DOCUMENTS

| EP | 3328286 A1 * | 6/2018 | ......... A61B 10/0096 |
| IT | 2015UB2656 A1 * | 10/2015 | ......... A61B 10/0096 |
| WO | WO-2016079611 A1 * | 5/2016 | ......... A61B 10/0096 |

* cited by examiner

Primary Examiner — Holly Kipouros

(57) ABSTRACT

A container (1) for in vitro diagnostic has a lower receptacle (2) designed to contain a non-toxic liquid (LS), an upper receptacle (3) designed to contain a toxic liquid (LF), and a connecting sleeve (4), in a threaded coupling with the lower receptacle (2) and the upper receptacle (3) for butt joining them. The connecting sleeve (4) has a transversal septum (40) being provided with a plurality of passage openings (48) and vent openings (49). When the container (1) is completely closed, both the lower receptacle (2) and the upper receptacle (3) abut the transversal septum (40). If the upper receptacle (3) is partially unscrewed with respect to the transversal septum (40), the toxic liquid (LF) flows by gravity into the lower receptacle (2). A method for storing a sample of human or animal tissue by using the container (1) is also provided.

13 Claims, 7 Drawing Sheets

CONTAINER AND METHOD FOR PRESERVING A TISSUE SAMPLE

TECHNICAL FIELD

The present invention relates to a container for in vitro diagnostic. The invention can be used, more specifically, in diagnostic histopathology. The container is of the single use type. The invention also relates to a method for storing and transporting a sample of human or animal tissue.

BACKGROUND ART

More in detail, such a container is used for the secure fixation, storage and transport of human or animal tissues or parts thereof to be subjected to specific histological, immunohistochemical and molecular biology laboratory tests. The tissue samples taken in vivo are immersed in a suitable fixative-preservative reagent in order to inhibit degradation processes and keep the architectural and macromolecular structure of the tissues intact.

To date, liquids containing formaldehyde in buffered solution are considered optimal fixative-preservatives. In the diagnostic routine it is evident that the major problem in the use of formaldehyde is the containment of risks to the health of the operators, since formaldehyde was classified according to EU regulation 1272/2008 as an "Acute Tox 3" substance—substance with acute Category 3 toxicity by ingestion, skin contact and inhalation, and as a "Canc 2" substance—carcinogenic suspected substance. The recent new regulation, which integrated the previous one, reclassified formaldehyde as "Carc. 1B"—presumed or certain carcinogenic substance, and "Muta 2"—substance suspected of causing genetic alterations.

International patent application WO 2017/016676 describes a container for storing and transporting a tissue sample to be subjected to histological examination. According to said patent application, a lower receptacle containing a buffer solution is closed with an internally threaded cap. The cap has superiorly a cylindrical seat having a base, provided with through holes and orthogonal tips pointing upwards, and a wall provided with an outer circumferential projection. A capsule, containing formaldehyde, sealed by a protective film, has an external thread. A ring nut is hooked to the outer circumferential projection of the cap cylindrical seat, and the sealed capsule is screwed onto its internal thread. As the capsule approaches the base of the cap cylindrical seat, the tips of the cylindrical seat pierce the protective film, and the formaldehyde passes through the cap to mix with the buffer solution, in which the tissue sample has been placed.

The formaldehyde flows from the upper receptacle to the lower receptacle along the through holes made in the base of the cap; there is a drawback that the air, present in the lower receptacle, having to pass into the upper receptacle, hinders the passage of the formaldehyde.

The container described in the aforementioned international patent application has four component parts, i.e. the lower receptacle, the cap, the capsule and the ring nut.

The packaging of the container complete with formaldehyde for its subsequent use requires the sealing of the capsule by means of the protective film and the provision of the piercing tips on the cap.

In addition to air, the pierced film can create an obstacle to the passage of the formaldehyde from the upper receptacle to the lower receptacle.

US 2009/0100944 discloses a container for storing a biological sample, comprising a first chamber for receiving a sample holder, a second chamber and a closure. A valve isolates the first chamber from the second one or puts them in fluid communication.

US 2011/0060137 discloses a method and a container for the treatment of a stool sample.

The prior art document closest to the present invention is considered WO 2017/016676.

SUMMARY OF INVENTION

The invention aims to overcome the drawbacks of the prior art.

An object of the present invention is to minimize risks of exposure, through both contact and inhalation, to the fixative-preservative reagent typically containing formaldehyde, and to other toxic or harmful substances during the transfer and deposition of the tissue into the diagnostic container in vitro.

Another object of the invention is to provide a container for in vitro diagnostic in order to store and transport a tissue sample to be subjected to histopathological examinations in which the quantity or concentrations of the solutions to be inserted in the upper and lower receptacles vary in proportion.

A further object of the invention is to allow a direct introduction into the container with the ready and perfect detachment of the tissue sample from the sampling instrument or any transfer instrument carrying the sample, being used in such a way as to maintain the same structural architecture of the tissue to be examined for an optimal diagnosis.

Yet another object of the invention is to provide a container with a reduced number of component parts.

An additional object of the invention is to provide a container complete with a formaldehyde solution which does not require sealing of the capsule by means of a protective film and the provision of tips for piercing the protective film.

Connected to the previous object is an object to avoid the presence in the container of shredded film scraps that can create an obstacle to the passage of the formaldehyde solution from the upper receptacle to the lower receptacle.

Another important object is to provide a method of using the container with the aforementioned purposes that is intuitive and leaves small chance of error by those who work for storing and transporting a tissue sample to be subjected to histopathological examinations.

Therefore, in a first aspect thereof, the present invention provides a container for in vitro diagnostic according to claims 1 to 10.

In a second aspect thereof, the invention provides a method for storing a human or animal tissue sample according to claim 11.

BRIEF DESCRIPTION OF DRAWINGS

Further features and advantages of the invention will become most clear from the description of embodiments of the container in question, illustrated by way of an indicative and non-limiting example in the accompanying drawings, in which.

DESCRIPTION OF INVENTION EMBODIMENTS

Figure 1:
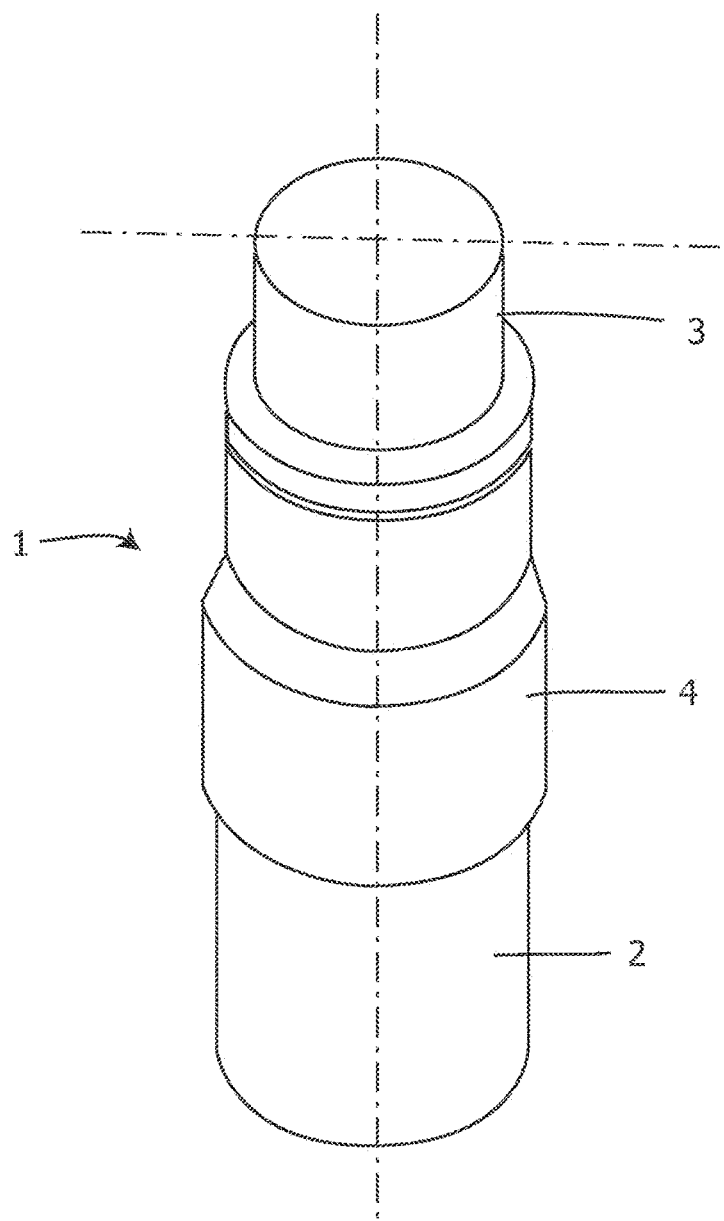
FIG. 1 is an overall perspective view of a first embodiment of the container according to the present invention.
Figure 2:
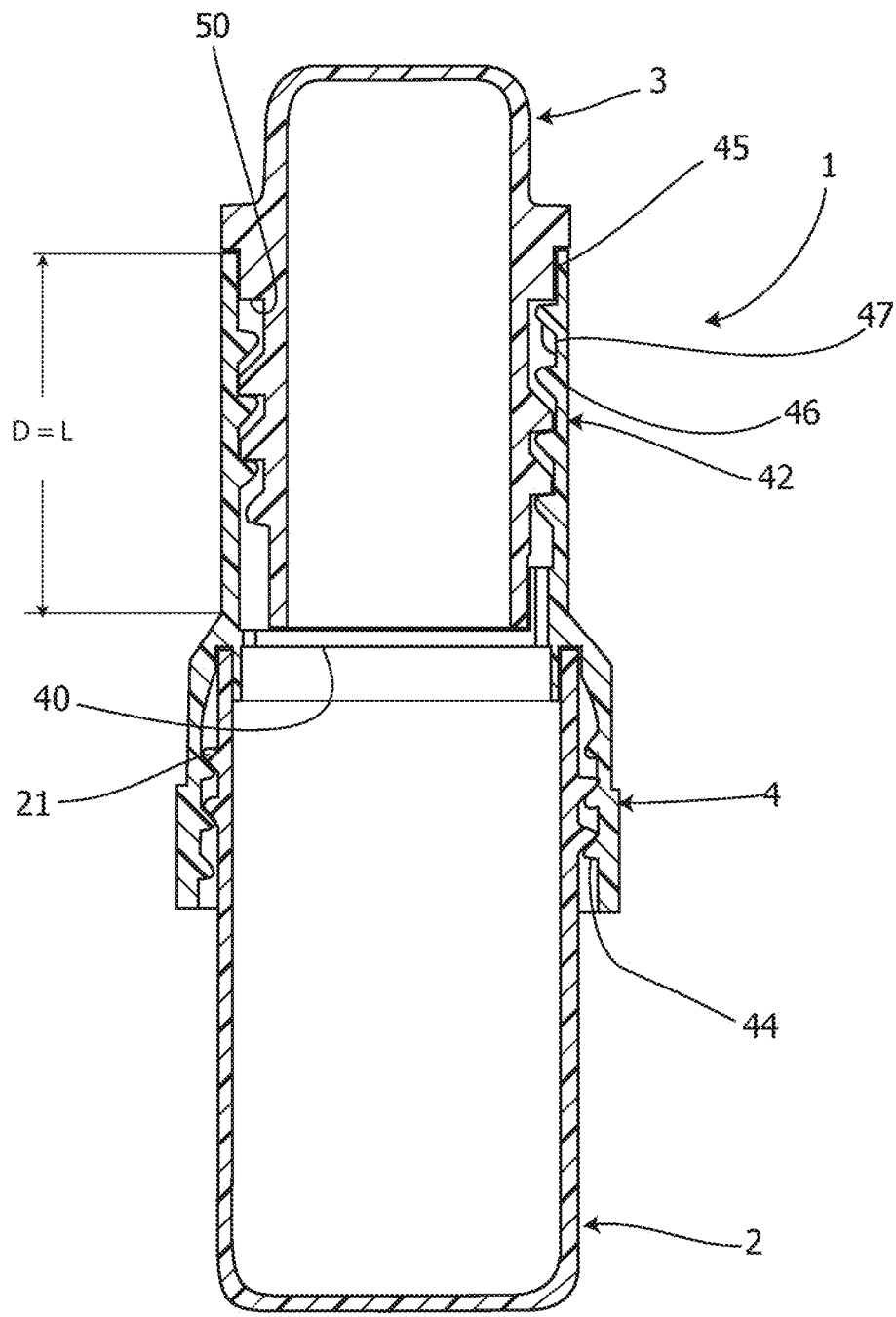
FIG. 2 is a central longitudinal sectional view of the container in FIG. 1, in a closed position.

First of all, reference is made to FIGS. 1 and 2 which are an overall perspective view and a central longitudinal sectional view in a closed position, respectively, of a first embodiment of the container 1 for in vitro diagnostic according to the present invention.

The container 1 consists of a lower receptacle 2, an upper receptacle 3 and a connecting sleeve 4, the latter as a threaded coupling means for joining the lower receptacle 2 to the upper receptacle 3. The terms "lower" and "upper" refer to the upright position of the container in its handling, because when the container is completely closed it can assume any position without any prejudice.

Figure 3:
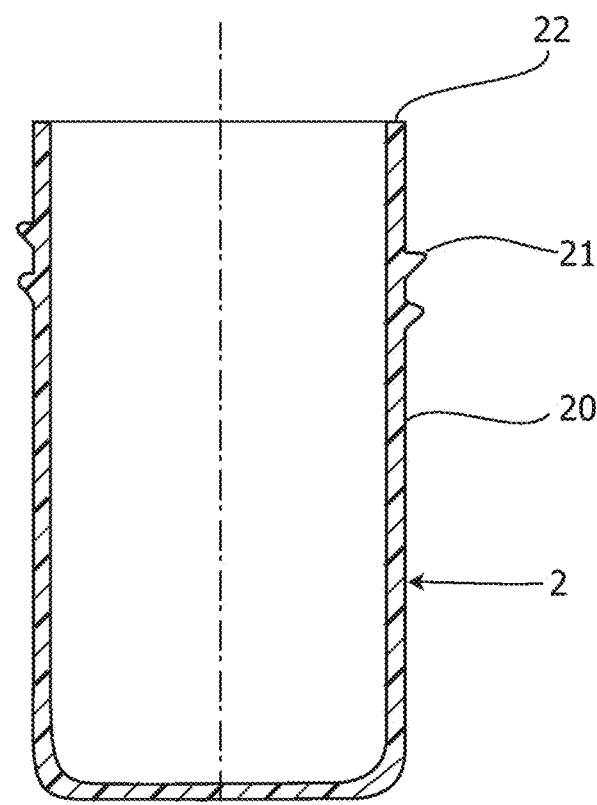
FIG. 3 is the central longitudinal sectional view of a lower receptacle in FIG. 1.

The lower receptacle 2 is designed to contain, before using the container, a non-toxic liquid, for example a buffer solution of the kind used to receive a tissue sample. As shown in the longitudinal sectional view in FIG. 3, the lower receptacle 2 has a side wall 20 provided with an external thread 21 and ending with a circular mouth 22.

The upper receptacle 3 is designed to contain, before using the container, a toxic liquid, for example a formaldehyde solution, useful for fixing and storing a tissue sample. Reference is made to the longitudinal sectional view in FIG. 4. The upper receptacle 3, shown inverted with respect to the overall sectional view in FIG. 2, has a side wall 30 provided with an external thread 31 and terminating with a circular mouth 32 of smaller diameter than that of the circular mouth 22 of the lower receptacle 2. An abutting step-shaped circumferential projection 33 is made in such a way that a horizontal plane of the step, indicated as 34, is located at a distance D from the circular mouth 32 of the upper receptacle 3.

Figure 5:
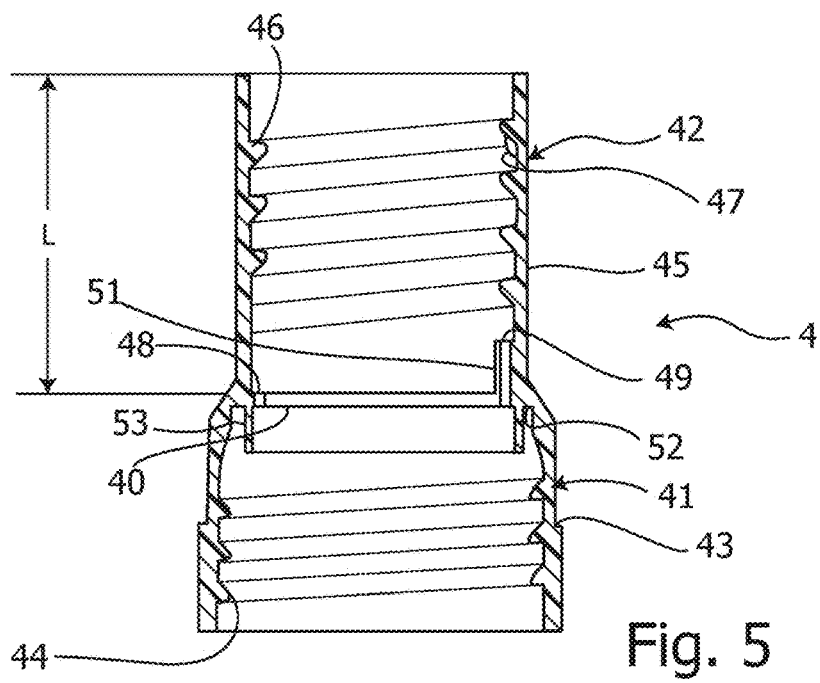
FIGS. 5 and 6 are the central longitudinal sectional view of a connecting sleeve between the lower receptacle and the upper receptacle in FIG. 2 and, respectively, a top plan view of the connecting sleeve.
Figure 6:
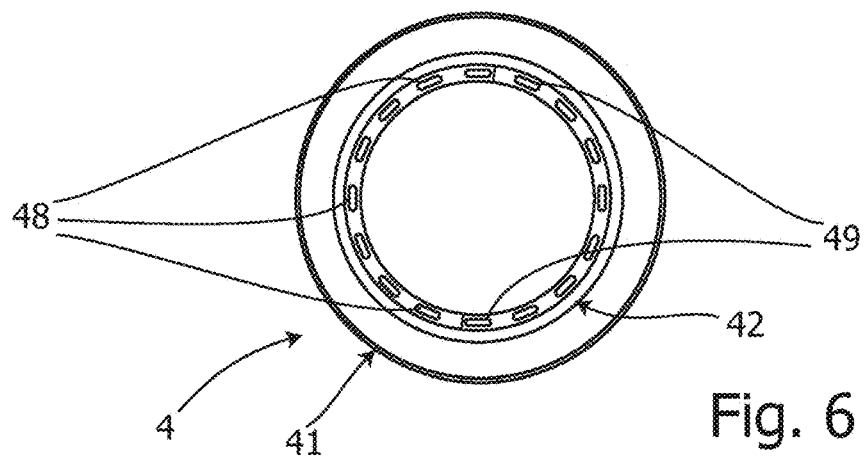

Reference is now made to FIGS. 5 and 6 which are the central longitudinal sectional view of the connecting sleeve 4 between the lower receptacle 2 and the upper receptacle 3 in FIG. 2 and a top plan view of the connecting sleeve 4, respectively.

The connecting sleeve 4, as shown in FIG. 2, engages longitudinally the external threads 21 and 31 of the lower receptacle 2 and upper receptacle 3, respectively, for the butt joint of said receptacles. The connecting sleeve 4 has a transversal septum 40 against which the lower receptacle 2 and the upper receptacle 3 with their respective circular mouths 22, 32 abut, on opposite sides, when the container 1 is completely closed.

It is therefore understood that the threaded coupling means between the lower receptacle 2 and the upper receptacle 3 according to the invention are constituted by the single connecting sleeve 4, comprising a lower portion 41 and an upper portion 42.

The lower portion 41 has a side wall 43 with an internal thread 44 engaging the external thread 21 of the lower receptacle 2. The upper portion 42 has a side wall 45 of a given length L with an internal thread 46 engaging the external thread 31 of the upper receptacle 3. The internal thread 46 of the upper portion 42 of the connecting sleeve 4 has a retaining projection 47 near the upper end of the upper portion 42 to limit the removal stroke of the circular mouth 32 of the upper receptacle 3 from the transversal septum 40 by unscrewing the upper receptacle 3.

The transversal septum 40 separates the lower portion 41 of the connecting sleeve 4 from its upper portion 42, and is provided with a plurality of passage openings in the form of holes 48 and vent openings in the form of slots 49, as will be explained below, with reference to FIG. 7 which is a perspective view of an enlarged detail of the transversal septum 40.

Figure 4:
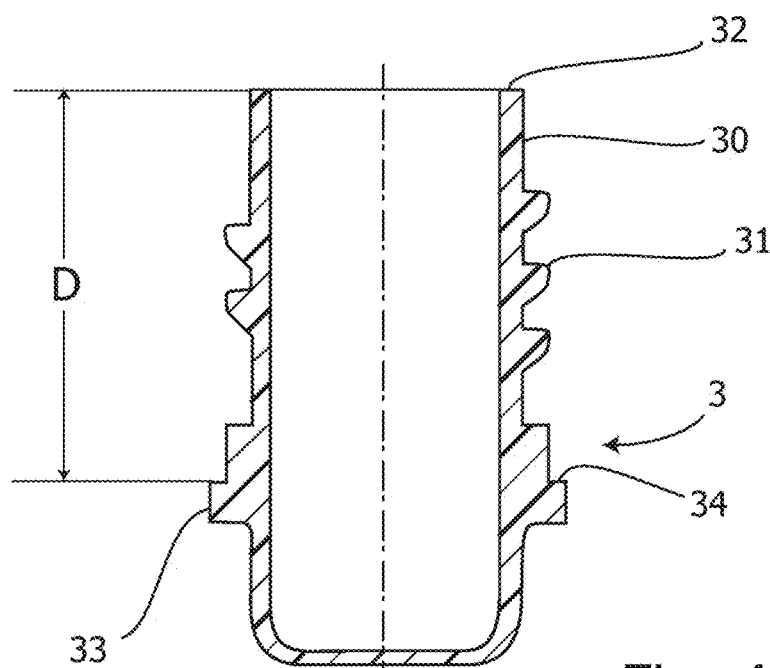
FIG. 4 is the central longitudinal sectional view of an upturned upper receptacle in FIG. 2.

As already mentioned, the upper receptacle 3 has, on its outer wall 30, an abutting step-shaped circumferential projection 33 that is made in such a way that the horizontal plane 34 of the step is at a distance D from the circular mouth 32, as shown in FIG. 4. Thanks to this geometric arrangement, the abutting step-shaped circumferential projection 33 allows the closure of an interspace 50 (FIG. 2) formed between the side wall 45 of the upper portion 42 of the connecting sleeve 4 and the side wall 30 of the upper receptacle 3. The distance D of the horizontal plane 34 of the abutting step of the projection 33 from the circular mouth 32 of the upper receptacle 3 is equal to the length L of the upper portion 42 of the connecting sleeve 4. The upper receptacle 3 is thus closed when it is fully screwed into the upper portion 42 of the connecting sleeve 4.

Figure 7:
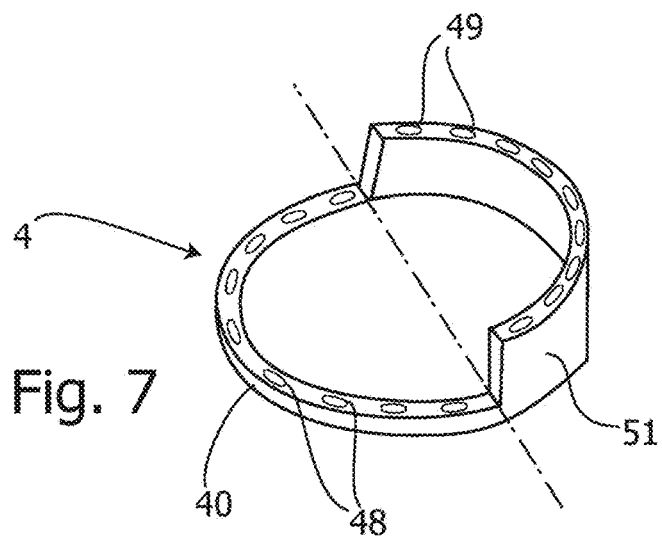
FIG. 7 is a perspective view of an enlarged detail of a transversal septum of the connecting sleeve in FIGS. 5 and 6.
Figure 8:
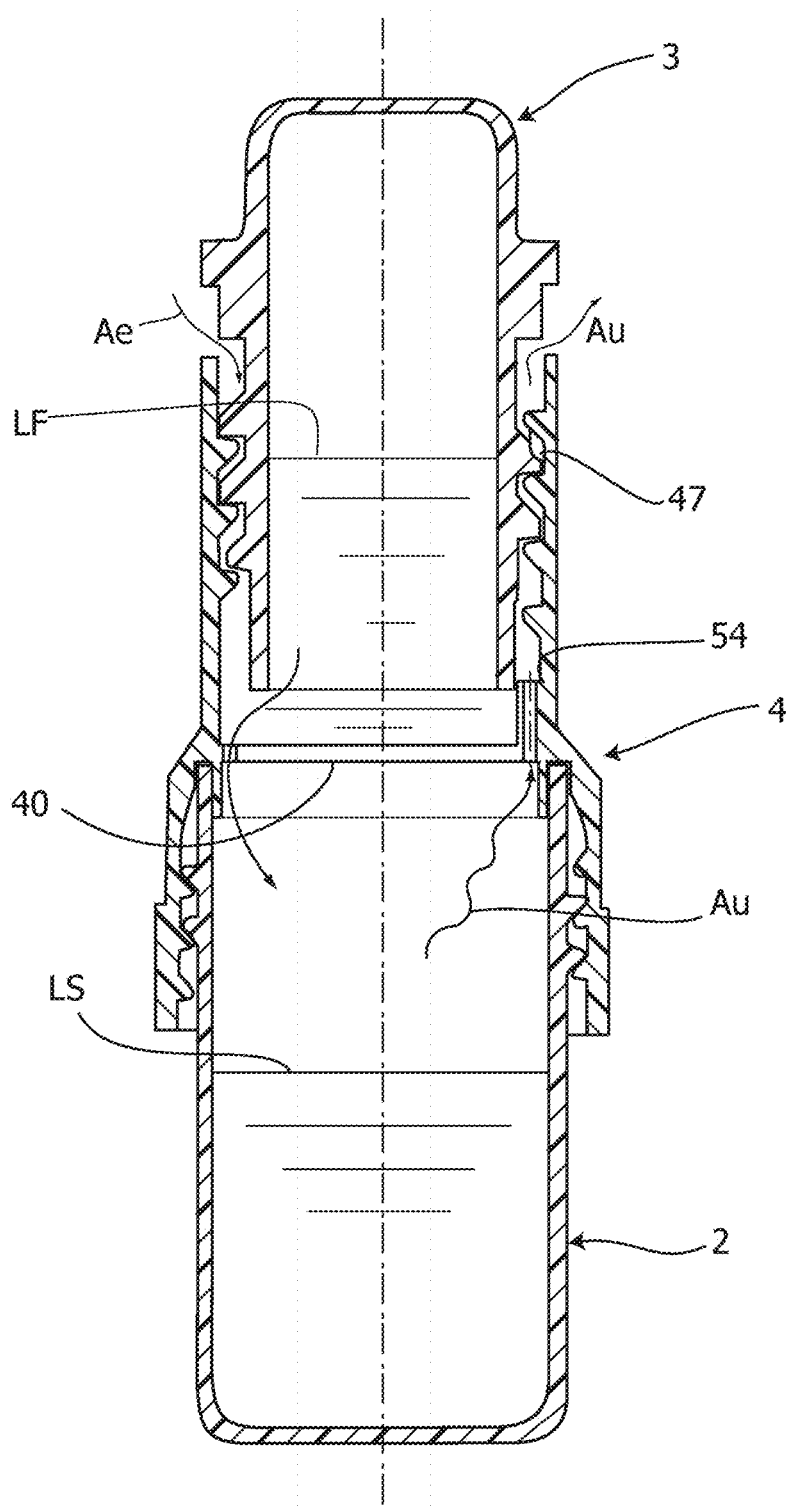
FIG. 8 is a central longitudinal sectional view similar to that in FIG. 1, partially open and provided with liquids.

Referring also to FIG. 7, it is seen that the plurality of passage openings of the transversal septum 40 comprise the multiplicity of through holes 48 made at the interspace 50 between the wall 45 of the upper portion 42 of the connecting sleeve 4. The through holes 48 permit the non-toxic liquid to flow from the upper receptacle 3 to the lower receptacle 2, as shown in FIG. 8 which is a central longitudinal sectional view of the container 1 similar to that of FIG. 1, but in a partially open position and provided with liquids. The liquid in the upper receptacle 3 is a toxic solution LF, for example based on formaldehyde, and the liquid LS in the lower receptacle 2 is a non-toxic buffer solution.

The lower receptacle 2 and the upper receptacle 3 can be supplied with the respective liquids before the container 1 is distributed for sale.

In the transversal septum 40, the multiplicity of through slots 49 for the escape of air from the lower receptacle 2 to the outside is made in a cylindrical portion 51 matching said interspace 50.

Comparing FIGS. 2 and 8, it can be understood that when the container is completely closed (FIG. 2), the upper receptacle 3 is sealed in that its circular mouth 32 hermetically abuts the transversal septum 40. At the same time, also the lower receptacle 2 is sealed because completely screwed into the lower portion 41 of the connecting sleeve 4 in a seat 52 (FIG. 5) created between a hollow cylindrical element 53 and the side wall 43 of the lower portion 41 of the connecting sleeve 4. The openings of the lower receptacle 2 consist of the through holes 48 and the venting slots 49, the latter facing the interspace 50. The interspace 50 is hermetically sealed by a cap formed by the upper receptacle 3 and its abutting step-shaped circumferential projection 33 on the upper portion 42 of the connecting sleeve 4.

If the upper receptacle 3 is unscrewed, air Ae begins to enter from the outside while the toxic liquid LF flows by gravity from the upper receptacle 3 across the through holes 48 into the lower receptacle 2. Air Au, present above the liquid LS in the lower receptacle 2, exits upwards through the venting slots 49. The venting slots 49 have an outlet orifice 54 which is above the maximum removal stroke of the upper receptacle 3 with respect to the transversal septum 40 which is limited by the retaining projection 47 provided in the internal thread 46 of the upper portion 42 of the connecting sleeve 4.

Figure 9:
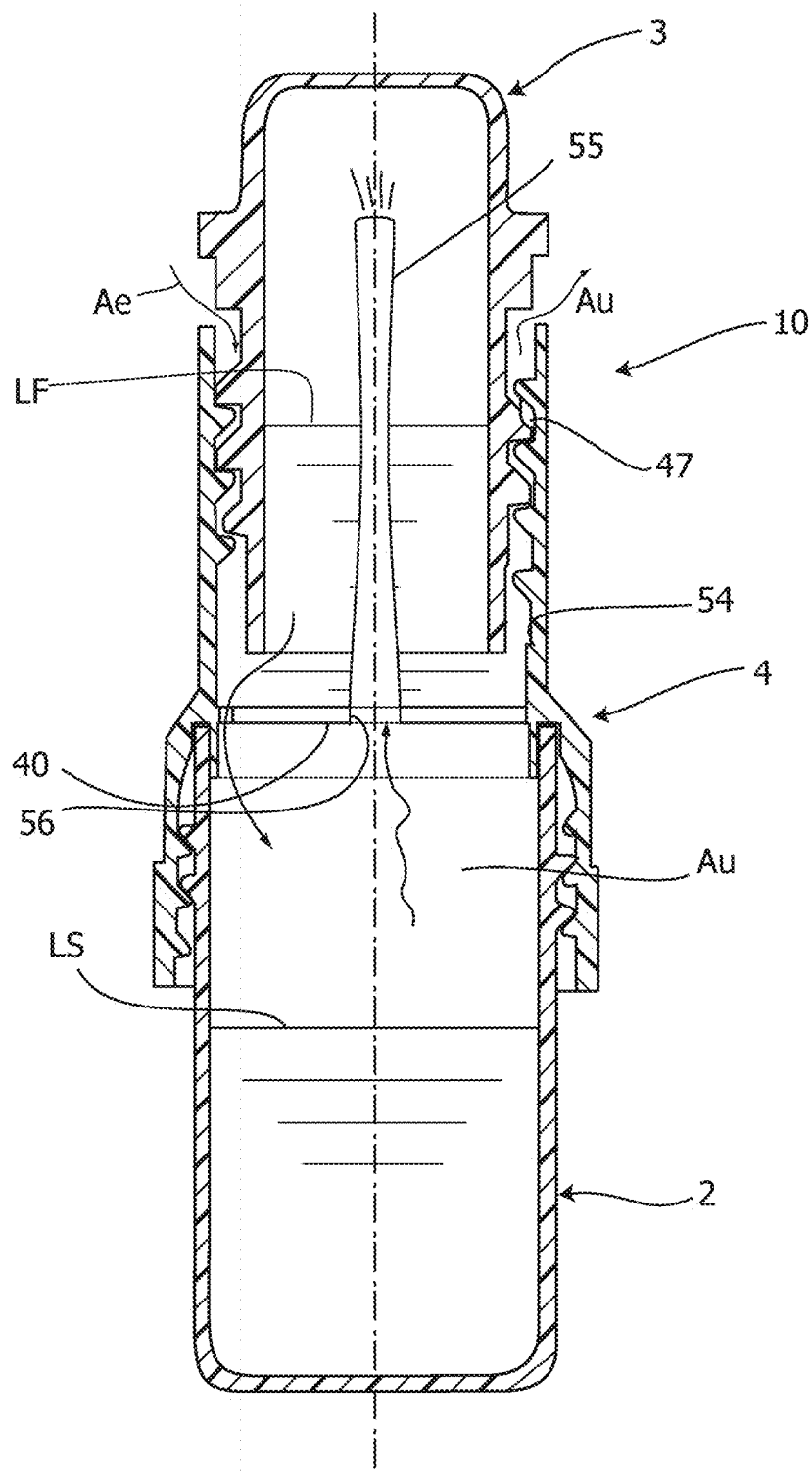
FIG. 9 is a central longitudinal sectional view, similar to that in FIG. 8, of a second embodiment of the container according to the invention, in a partially open position and provided with liquids.

It should be understood that, due to the embodiment of the container 1 described above, the vapor emissions of the toxic liquid LF are in a minimal amount constituted by their traces present in the air Au exiting the lower receptacle 2. To avoid this even slightest emission, a second embodiment of a container according to the invention is provided, which is shown in FIG. 9 similar to FIG. 8 of the first embodiment.

The container indicated as 10 has parts equal to those of the container 1 of the first embodiment, designated with the same reference numerals. The container 10 differs from the container 1 in that the at least one vent opening of the transversal septum 40 consists of at least one chimney element 55 adapted to connect the lower receptacle 2 with the interior space of the upper receptacle 3 above the toxic liquid LF contained therein. To achieve this, the chimney element 55 is made passing through the transverse partition 40 in a hole 56. The height of the chimney element 55 is greater than the height of the liquid level LF which can be stored in the upper receptacle 3. Thanks to this arrangement, there is neither escape of vapors from the container 10 during the passage of the toxic liquid LF from the upper receptacle 3 to the lower receptacle 2, nor subsequently when the container 10 is closed by screwing the upper receptacle 3 into the connecting sleeve 4 until its hermetic abutment with the transversal septum 40.

It should be evident that, when the upper receptacle 3 is in this position, the lower receptacle 2 can be unscrewed and separated from the connecting sleeve 4 and can also be reconnected thereto.

In order to maintain the hermetic closure of the container 1, 10, what is requested is not to unscrew the upper receptacle, except when the mixing of toxic and non-toxic liquids is foreseen, and especially in the absence of the lower receptacle. A safety seal (not shown in the drawings) can be provided that externally connects both the lower receptacle and the upper receptacle to the connecting sleeve.

Figure 10:
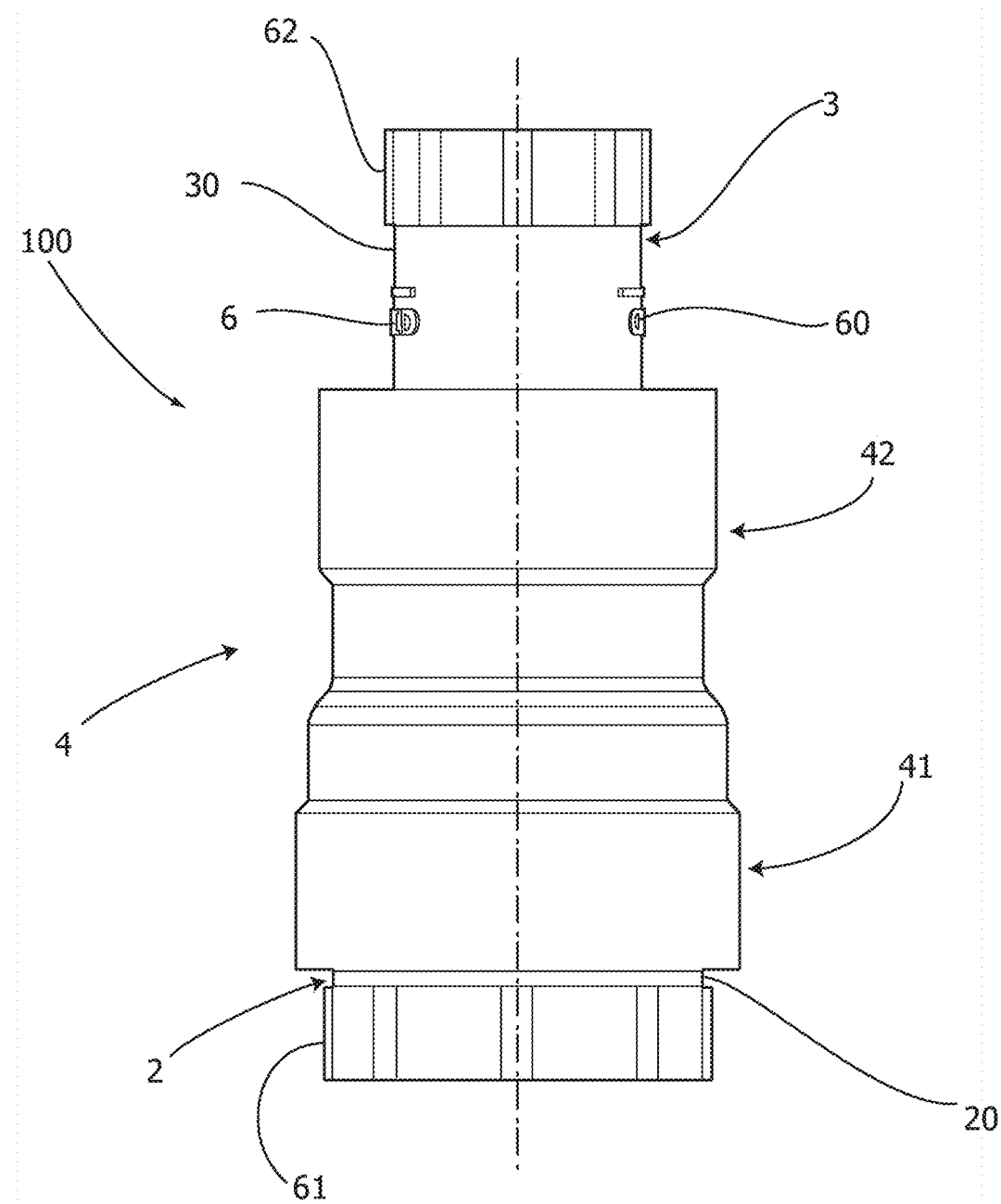
FIG. 10 is a side view of a customized variant of the container according to the present invention.

Alternatively, closure reference notches (not shown in the drawings) may be provided externally both on the lower receptacle and on the upper receptacle which match corresponding notches on the connecting sleeve. Further, arrows may also be provided indicating the opening and closing direction of the receptacles, as shown in the side view of the customized variant of the container 100 according to the present invention shown in FIG. 10. In this figure, also identical reference numerals indicate similar parts to those of other embodiments. In FIG. 10, designated as 6 and 60 are arrows and writings indicating the closing direction and the opening direction, respectively, of the upper receptacle 3, which is certainly the most critical for safety purposes.

To facilitate the unscrewing and screwing of the receptacles 2, 3, their side walls 20, 30 have near their ends a prismatic shape with a polygonal plan with rounded corners 61, 62, to improve their grip.

A method for storing a sample of human or animal tissue with the use of the container according to the present invention is now described.

Let us suppose that the lower receptacle 2 and the upper receptacle 3 are supplied with the non-toxic liquid and the toxic liquid, respectively, before the container is put into distribution for sale.

Once the container according to the invention is received, an operator, in order to storage a tissue sample for transport, unscrews the lower receptacle 2, containing the non-toxic liquid LS, from the connecting sleeve 4, introduces directly into the lower receptacle 2 the tissue sample, and screws down the lower receptacle 2 onto the connecting sleeve 4 so as to obtain a tight seal. According to the method of the present invention, the operator partially unscrews the upper receptacle 3 which is completely screwed into the connecting sleeve 4, with the circular mouth 32 sealed against the transversal septum 40. The unscrewing proceeds up to the retaining projection 47 in order to transfer the toxic liquid LF from the upper receptacle 3 to the lower receptacle 2 through the plurality of transfer openings, i.e. the holes 48, and to let the air contained in the lower receptacle 2 flow through the at least one vent opening, i.e. slots 49 in the first embodiment or the chimney element 55 in the second embodiment of the container according to the present invention. Once the two liquids, the non-toxic liquid LS of the lower receptacle 2 and the toxic liquid LF of the upper receptacle 3, have been mixed, the upper receptacle 3 is screwed tightly until its circular mouth 32 abuts the transversal septum 40, and the abutting step-shaped circumferential projection 33 of the same upper receptacle 3 abuts the upper portion 42 of the connecting sleeve 40.

The materials and the dimensions of the invention as described above, illustrated in the drawings and hereinafter claimed, may be any according to requirements. Furthermore, all the details can be replaced with other technically equivalent ones without thereby departing from the scope of the present patent application.

The invention claimed is:

1. A container (1; 10; 100) for in vitro diagnostic comprising:
   a lower receptacle (2) designed to contain, before using the container (1; 10; 100), a non-toxic liquid (LS), having a side wall (20) provided with an external thread (21) and ending with a circular mouth (22),
   an upper receptacle (3) designed to contain, before using the container (1; 10; 100), a toxic liquid (LF), having a side wall (30) provided with an external thread (31) and ending with a circular mouth (32) smaller in diameter than the circular mouth (22) of the lower receptacle (2), and
   threaded coupling means longitudinally engaging said external threads (21, 31) for a butt joint of the lower receptacle (2) with the upper receptacle (3),
   characterized in that the threaded coupling means consists of a single connecting sleeve (4), consisting of
      a transversal septum (40) against which the lower receptacle (2) and the upper receptacle (3) abut when the container (1; 10; 100) is completely closed,
      a lower portion (41) having a side wall (43) with an internal thread (44) engaging the external thread (21) of the lower receptacle (2), an upper portion (42) having a side wall (45) of a given length (L) with an internal thread (46) engaging the external thread (31) of the upper receptacle (3), the internal thread (46) of the upper portion (42) of the connecting sleeve (4) having a retaining projection (47) for limiting a removal stroke of the circular mouth (32) of the upper receptacle (3) from the transversal septum (40) of the connecting sleeve (4) by partial unscrewing of the upper receptacle (3);

the transversal septum (40) separating the lower portion (41) of the connecting sleeve (4) from its upper portion (42) and being provided with a plurality of passage openings and at least one vent opening;

the upper receptacle (3) having on its side wall (30) an abutting step-shaped circumferential projection (33) with a horizontal plane (34) for closing an interspace (50) formed between the side wall (45) of the upper portion (42) of the connecting sleeve (4) and the side wall (30) of the upper receptacle (3), a distance (D) of the horizontal plane (34) of the step-shaped circumferential projection (33) from the circular mouth (32) of the upper receptacle (3) being equal to said length (L) of the upper portion (42) of the connecting sleeve (4), in order to simultaneously close the lower receptacle (2) and the upper receptacle (3) when both are completely screwed into the respective lower portion (41) and upper portion (42) of the connecting sleeve (4).

2. The container (1; 10; 100) according to claim 1, wherein the plurality of passage openings of the transversal septum (40) are a plurality of through holes (48) made at said interspace (50) for the passage of the toxic liquid (LF) from the upper receptacle (3) to the lower receptacle (2).

3. The container (1) according to claim 1, wherein the at least one vent opening in the transversal septum (40) is a plurality of through slots (49) for the escape of air from the lower receptacle (2) to the outside, an outlet orifice (54) of each of the plurality of through slots (49) being above a maximum removal stroke position of the upper receptacle (3) with respect to the transversal septum 40.

4. The container (1; 10; 100) according to claim 1, wherein said non-toxic liquid (LS) is a preservative solution for a tissue sample suitable for allowing its detachment from a transfer instrument, and said toxic liquid (LF) is a fixative-preservative solution.

5. The container (1; 10; 100) according to claim 1, wherein the lower receptacle (2) is unscrewable and separable from the connecting sleeve (4) and reconnectable thereto.

6. The container (1; 10; 100) according to claim 1, wherein the lower receptacle (2) and the upper receptacle (3) are provided with non-toxic liquid (LS) and toxic liquid (LF), respectively, before that the container (1; 10; 100) is distributed for sale.

7. The container (1; 10; 100) according to claim 6, wherein a safety seal externally joins both the lower receptacle (2) and the upper receptacle (3) to the connecting sleeve (4) at the time of its distribution.

8. The container (100) according to claim 6, wherein closing and opening reference marks (6, 60) are provided externally on the upper receptacle (3) for opening and closing the container (100).

9. The container (100) according to claim 1, wherein the side walls (20, 30) of the lower and upper receptacle (2, 3) have their ends of a prismatic shape with a polygonal plan with rounded corners (61, 62).

10. The container (10; 100) according to claim 1, further comprising at least one chimney element (55) passing through the transversal septum suitable to put in communication the lower receptacle (2) with the inner space of the upper receptacle (3) above the toxic liquid (LF) contained therein.

11. A container (1; 10; 100) for in vitro diagnostic comprising:

a lower receptacle (2) designed to contain, before using the container (1; 10; 100), a non-toxic liquid (LS), having a side wall (20) provided with an external thread (21) and ending with a circular mouth (22), an upper receptacle (3) designed to contain, before using the container (1; 10; 100), a toxic liquid (LF), having a side wall (30) provided with an external thread (31) and ending with a circular mouth (32) smaller in diameter than the circular mouth (22) of the lower receptacle (2), and threaded coupling means longitudinally engaging said external threads (21, 31) for a butt joint of the lower receptacle (2) with the upper receptacle (3), and having a transversal septum (40) against which the lower receptacle (2) and the upper receptacle (3) abut when the container (1; 10; 100) is completely closed, characterized in that the threaded coupling means comprises a single connecting sleeve (4), comprising a lower portion (41) having a side wall (43) with an internal thread (44) engaging the external thread (21) of the lower receptacle (2), an upper portion (42) having a side wall (45) of a given length (L) with an internal thread (46) engaging the external thread (31) of the upper receptacle (3), the internal thread (46) of the upper portion (42) of the connecting sleeve (4) having a retaining projection (47) for limiting a removal stroke of the circular mouth (32) of the upper receptacle (3) from the transversal septum (40) of the connecting sleeve (4) by partial unscrewing of the upper receptacle (3);

the transversal septum (40) separating the lower portion (41) of the connecting sleeve (4) from its upper portion (42) and being provided with a plurality of passage openings and at least one vent opening;

the upper receptacle (3) having on its side wall (30) an abutting step-shaped circumferential projection (33) with a horizontal plane (34) for closing an interspace (50) formed between the side wall (45) of the upper portion (42) of the connecting sleeve (4) and the side wall (30) of the upper receptacle (3), a distance (D) of the horizontal plane (34) of the step-shaped circumferential projection (33) from the circular mouth (32) of the upper receptacle (3) being equal to said length (L) of the upper portion (42) of the connecting sleeve (4), in order to simultaneously close the lower receptacle (2) and the upper receptacle (3) when both are completely screwed into the respective lower portion (41) and upper portion (42) of the connecting sleeve (4), wherein the at least one vent opening of the transversal septum (40) consists of at least one chimney element (55) suitable to put in communication the lower receptacle (2) with the inner space of the upper receptacle (3) above the toxic liquid (LF) contained therein.

12. A method for storing a sample of human or animal tissue by using a container (1; 10; 100) for in vitro diagnostic comprising:

a lower receptacle (2) designed to contain, before using the container (1; 10; 100), a non-toxic liquid (LS), having a side wall (20) provided with an external thread (21) and ending with a circular mouth (22), an upper receptacle (3) designed to contain, before using the container (1; 10; 100), a toxic liquid (LF), having a side wall (30) provided with an external thread (31) and ending with a circular mouth (32) smaller in diameter than the circular mouth (22) of the lower receptacle (2), and threaded coupling means longitudinally engaging said external threads (21, 31) for a butt joint of the lower receptacle (2) with the upper receptacle (3), and having a transversal septum (40) against which the lower receptacle (2) and the upper receptacle (3) abut when the container (1; 10; 100) is completely closed, characterized in that the threaded coupling means comprises a single connecting sleeve (4), comprising a lower portion (41) having a side wall (43) with an internal thread (44) engaging the external thread (21) of the lower receptacle (2), an upper portion (42) having a side wall (45) of a given length (L) with an internal thread (46) engaging the external thread (31) of the upper receptacle (3), the internal thread (46) of the upper portion (42) of the connecting sleeve (4) having a retaining projection (47) for limiting a removal stroke of the circular mouth (32) of the upper receptacle (3) from the transversal septum (40) of the connecting sleeve (4) by partial unscrewing of the upper receptacle (3);

the transversal septum (40) separating the lower portion (41) of the connecting sleeve (4) from its upper portion (42) and being provided with a plurality of passage openings and at least one vent opening;

the upper receptacle (3) having on its side wall (30) an abutting step-shaped circumferential projection (33) with a horizontal plane (34) for closing an interspace (50) formed between the side wall (45) of the upper portion (42) of the connecting sleeve (4) and the side wall (30) of the upper receptacle (3), a distance (D) of the horizontal plane (34) of the step-shaped circumferential projection (33) from the circular mouth (32) of the upper receptacle (3) being equal to said length (L) of the upper portion (42) of the connecting sleeve (4), in order to simultaneously close the lower receptacle (2) and the upper receptacle (3) when both are completely screwed into the respective lower portion (41) and upper portion (42) of the connecting sleeve (4), wherein the lower receptacle (2) and the upper receptacle (3) are provided with non-toxic liquid (LS) and toxic liquid (LF), respectively, before that the container (1; 10; 100) is distributed for sale, the method comprising the steps of unscrewing the lower receptacle (2) containing the non-toxic liquid (LS) from the connecting sleeve (4), directly introducing the sample of human or animal tissue into the lower receptacle (2), screwing the lower receptacle (2) onto the connecting sleeve (4) so as to obtain a seal, characterized by the following steps:

unscrewing the upper receptacle (3) in the connecting sleeve (4) up to the retaining projection (47) so as to transfer the toxic liquid (LF) into the lower receptacle (2) through the plurality of passage openings and to let air contained in the lower receptacle (2) flow through the at least one vent opening;

hermetically screwing down the upper receptacle (3) until the circular mouth (32) of the upper receptacle (3) abuts the transversal septum (40) and simultaneously the abutting step-shaped circumferential projection (33) of the upper receptacle (3) abuts the upper portion (42) of the connecting sleeve (4).

13. A method for storing a sample of human or animal tissue by using the container according to claim 6, comprising the steps of unscrewing the lower receptacle (2) containing the non-toxic liquid (LS) from the connecting sleeve (4), directly introducing the sample of human or animal tissue into the lower receptacle (2), screwing the lower receptacle (2) onto the connecting sleeve (4) so as to obtain a seal, characterized by the following steps:

unscrewing the upper receptacle (3) in the connecting sleeve (4) up to the retaining projection (47) so as to transfer the toxic liquid (LF) into the lower receptacle (2) through the plurality of passage openings and to let air contained in the lower receptacle (2) flow through the at least one vent opening;

hermetically screwing down the upper receptacle (3) until the circular mouth (32) of the upper receptacle (3) abuts the transversal septum (40) and simultaneously the abutting step-shaped circumferential projection (33) of the upper receptacle (3) abuts the upper portion (42) of the connecting sleeve (4).

* * * * *